Patent Number: 4,832,950

Date of Patent: May 23, 1989

United States Patent [19]
Takaya et al.

[54] ANTIMICROBIAL SUSPENSIONS AND ANTIMICROBIAL HAIR TREATMENT COMPOSITIONS

[75] Inventors: Susumu Takaya, Funabashi; Hajime Hirota; Motoko Nakamura, both of Tokyo, all of Japan

[73] Assignee: Kao Corporation, Tokyo, Japan

[21] Appl. No.: 193,186

[22] Filed: May 10, 1988

Related U.S. Application Data

[63] Continuation of Ser. No. 767,849, Aug. 21, 1985, abandoned.

[30] Foreign Application Priority Data

Aug. 29, 1984 [JP] Japan ................. 59-179978
Dec. 24, 1984 [JP] Japan ................. 59-272529
Dec. 27, 1984 [JP] Japan ................. 59-276789

[51] Int. Cl.⁴ .......................... A61K 7/06; A61K 7/08; A61K 31/78
[52] U.S. Cl. ............................ 424/81; 424/70; 514/188; 514/852; 514/880; 514/881
[58] Field of Search .......... 424/70, 81; 514/188, 514/852, 880, 881

[56] References Cited

U.S. PATENT DOCUMENTS

| | | | |
|---|---|---|---|
| 3,236,733 | 2/1966 | Karsten et al. | 514/188 |
| 3,489,686 | 1/1970 | Parran, Jr. | 514/166 |
| 3,580,853 | 5/1971 | Parran, Jr. | 424/78 |
| 3,636,213 | 1/1972 | Gerstein et al. | 514/188 |
| 3,723,325 | 3/1973 | Parran, Jr. | 424/78 |
| 3,753,916 | 8/1973 | Parran, Jr. | 424/78 |
| 3,761,417 | 9/1973 | Parran, Jr. | 424/78 |
| 3,761,418 | 9/1973 | Parran, Jr. | 424/78 |
| 3,940,482 | 2/1976 | Grand | 514/188 |
| 4,210,654 | 7/1980 | Bauer et al. | 514/644 |
| 4,323,683 | 4/1982 | Bolich, Jr. et al. | 546/6 |
| 4,345,080 | 8/1982 | Bolich, Sr. | 424/70 |
| 4,379,753 | 4/1983 | Bolich, Jr. | 424/70 |
| 4,529,587 | 7/1985 | Green | 514/846 |
| 4,557,928 | 12/1985 | Glover | 514/166 |
| 4,670,430 | 6/1987 | Imamura et al. | 424/70 |

FOREIGN PATENT DOCUMENTS

| | | |
|---|---|---|
| 7704 | 2/1980 | European Pat. Off. |
| 0034846 | of 1981 | European Pat. Off. |
| 60611 | 9/1982 | European Pat. Off. |
| 93541 | 11/1983 | European Pat. Off. |
| 53-097010 | 8/1978 | Japan |
| 56-061308 | 5/1981 | Japan |
| 1051268 | 12/1966 | United Kingdom |

OTHER PUBLICATIONS

Sagarin, *Cosmetics Science & Technology*, 159, 403–408 (1957).
*Handbook of Non-Prescription Drugs*, pp. 406–407 (1979).
Derwent Abstract 90573.

*Primary Examiner*—Dale R. Ore
*Attorney, Agent, or Firm*—Oblon, Fisher, Spivak, McClelland & Maier

[57] ABSTRACT

A polyvalent metal salt of 2-mercaptopyridine-N-oxide (Mept compound) is dispersed in water by aid of a specific dispersant selected from the group consisting of (A), (B) and (C):

(A) A polyglycol/polyamine condensation polymer, polyglycol/polyamine/alkylamine condensation polymer or alkyleneamine condensation polymer;

(B) At least one water-soluble polymer compound selected from the group consisting of hydroxyalkylcelluloses and partly quaternarized products thereof, and at least one non-ionic surfactant;

(C) At least one cationic polymer compound and at least one inorganic salt.

The resulting suspension has improved stability and is applicable to shampooes, hair rinses and the like.

10 Claims, No Drawings

ANTIMICROBIAL SUSPENSIONS AND ANTIMICROBIAL HAIR TREATMENT COMPOSITIONS

This application is a continuation of Ser. No. 767,849 filed Aug. 25,1985 now abandoned.

BACKGROUND OF THE INVENTION (i) Field of the Invention

This invention relates to aqueous suspensions of antimicrobial agents and antimicrobial hair treatment compositions in which fine particulate polyvalent metal salts of 2-mercaptopyridine-N-oxide (which may be hereinafter referred to simply as Mept compounds) having a specific size distribution are stably dispersed.

(ii) Description of the Prior Art

Polyvalent metal salts of 2-mercaptopyridine-N-oxide are known to be effective as antimicrobials and are widely utilized not only as ordinary antimicrobials, but also as anti-dandruff agents and are incorporated into shampoo compositions, hair rinse compositions and the like. The polyvalent metals of the Mept compounds are magnesium, barium, strontium, zinc, cadmium, tin, zirconium and the like. Of these, zinc salts are widely used.

However, these Mept compounds are sparingly soluble in water, for instance, the zinc salt (hereinafter referred to simply as Zpt compounds) has a solubility in water of 15 ppm at 25° C. Accordingly, when they are incorporated into shampoo or hair rinse compositions, they must be utilized in a form of dispersions.

However, because of the considerable difference between the specific gravities of Zpt compounds (specific gravity =1.8) and a medium liquid for dispersion, the Zpt compounds are apt to settle and separate as time passes, and thus it was difficult to obtain a stable dispersion system containing Zpt compounds.

In order to prevent such settlement or separation, the following methods are known:

(i) Make the static viscosity of the dispersion medium high.

(ii) Make the particle size of Mept compounds so small that Brownian movemett will be dominant in the system.

By either method, settlement will be made difficult to take place.

Examples of method (i) are a method of adding viscosity increasing polymers such as cross-linked polyacrylates (Japanese Patent Publication No. 49-49117) and a method of adding acrylic acid/acrylate copolymers (Japanese Patent Publication No. 54-16951). However, these methods have the drawback that limitation is placed on the type of surface active agent usable to stably disperse Mept compounds.

As for method (ii), since Mept compounds having very small particle size are difficult to be produced, compositions containing fine particulate Mept compounds stably dispersed therein have not been practically obtained.

Under such conditions, the present inventors formerly made a study and succeeded in manufacturing Mept compounds having very small particle size (hereinafter referred to as fine particulate Mept compounds) compared with conventional Mept compounds incorporated into shampoo or hair rinse compositions (Japanese Patent Application Nos. 58-122845, 58-122846 and 59-82690).

The present inventors made further study in order to obtain stable antimicrobial suspensions making use of thus obtained fine particulate Mept compounds, and found that fine particulate Mept compounds are very sensitive to conditions of liquid media for dispersion and are apt to coagulate, leading to difficulty in keeping the original size distribution. More specifically, the following phenomena were noted.

(1) Fine particulate Mept compounds in a suspension coagulate when electrolytes such as salts are included in the suspension, or when the suspension is got frozen or heated.

(2) Fine particulate Mept compounds are apt to coagulate when they are incorporated into hair treatment compositions such as shampooes o hair rinses in which surfactants are contained, because the surfactant per se is an electrolyte.

In order to prevent the coagulation of fine particulate Mept compounds, surface modification or colloidal protection have been proposed.

Examples of adding a water-soluble polymer to a shampoo composition which incorporates Mept compounds are disclosed in Japanese Patent Publication Nos. 47-20635 and 50-22044, in which cationic polymers are used as a water-soluble polymer in order to enhance the adsorption of Mept compounds to the hair and head skin. However, the cationic polymers function as a coagulating agent for fine particulate Mept compounds having a specific size distribution, and produce considerable coagulation.

The method of forming colloid layer of cellulose-type water-soluble polymers for protection also has a drawback in that the cellulose polymers coagulate when they form a colloidal adsorption layer on a particle to be protected. For instance, additinn of an aqueous solution of hydroxyalkylcellulose or the like, which is referred to in Japanese Patent Application Laid-Open Nos. 53-14710, 53-14711, 53-97010 and 57-176906, results in losing the original size distribution, leading to losing the stable dispersability.

From this reason, conventional art was directed to make use of cellulose-type water-soluble polymers as a thickner to enhance the viscosity of shampoo base thereby allowing the incorporated fine particulate Mept compounds to settle more slowly, or further incorporating swelling clay or pearling agent in order to give structual viscosity to the system of the shampoo composition, thereby preventing settlement of Mept compounds. Such methods cannot avoid limitations to surfactants to be incorporated into a shampoo base or viscosity of the shampoo base.

Preparation of hair rinse compositions or hair conditioning compositions is also accompanied by the limitation to viscosity of the composition in the case where fine particulate Mept compounds are incorpoarted into the compositions. Namely, the bases are limited to a highly viscous ones such as of emulsion system or gel.

SUMMARY OF THE INVENTION

In view of the above, the present inventors have further made an earnest study in order to overcome such problems, and have found that when fine particulate Mept compounds are dispersed in water by aid of a specific dispersant, the resulting suspension is excellent in that it is highly stable under the ordinary storage conditions, is superior in resistivity to salts, and, even frozen, can be restored to the state before frozen if only heated to melt. Surprisingly, it was also found that when thus prepapred aqueous dispersion of fine particulate Mept compounds was incorporated into a base of hair treatment compositions such as shampooes, hair rinses and hair lotions, the dispersion state of fine particulate Mept compounds could be maintained stably being free from limitations to storage conditions or to surfactants to be used in combination.

Accordingly, this invention consists of a first invention which relates to an antimicrobial suspension characterized by comprising a fine particulate polyvalent metal salt of 2-mercaptopyridine-N-oxide having a size distribution in which particles having a size below 0.2 micron are contained in amounts not smaller than 50 wt % and a dispersant selected from the group consisting of (A), (B) and (C):

(A) A polyglycol/polyamine condensation polymer or a polyglycol/polyamine/alkyl or alkyleneamine condensation polymer;

(B) At least one water-soluble polymer compound selected from the group consisting of hydroxyalkylcelluloses and partly quaternarized products thereof, and at least one non-ionic surfactant;

(C) At least one cationic polymer compound and at least one inorganic salt, and a second invention which relates to an antimicrobial hair treatment composition in which a hair treatment base thereof is incorporated with the antimicrobial suspension.

BRIEF DESCRIPTION OF THE DRAWING

The sole FIGURE is a graph showing relation between particle size of fine particulate Zpt and Amizet 5C.

DETAILED DESCRIPTION OF THE INVENTION AND PREFERRED EMBODIMENTS

The Mept compounds according to the invention are represented by the following general formula:

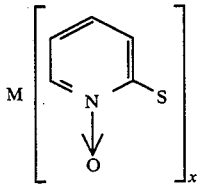

wherein M represents a polyvalent metal atom and x represents the atomic value of M.

Examples of the polyvalent metal atom, M includes magnesium, barium, strontium, zinc, cadmium, tin and zirconium. Of these, zinc salt of 2-mercaptopyridine-N-oxide is preferred.

The fine particulate Mept compounds to be used in the prssent invention have a size distribution in which not smaller than 50 wt % of the particles have a size of 0.2 micron or less. Preferably, the fine particulate metal salts have such a size distribution that particles having a size ranging from 0.5 to 1.0 micron are contained in amounts not larger than 15wt %, and particles having a size not smaller than 1.0 micron are contained 2 wt % or less. The fine particulate Mept compounds having such size dittribution can be prepared by any of the following methods:

(1) Method of utilizing a shear force of rigid body media such as glass beads having a particle size not larger than 0.5 mm, with which Mept compounds are agitated thereby obtaining fine powder (Japanese patent Applicaiion No. 58-122845).

(2) Method of reacting a monovalent water-soluble salt of 2-mercaptopyridine-N-oxide and an water-soluble polyvalent metal salt in the presence of an water-soluble compound having a basic nitrogen atom in a molecular thereof under hhe condition of pH 3 to 7, or optionally, further proceeding this reaction in the presence of a water-soluble compound having hydroxy group under a temperature of not higher than 0° C. (Japanese Patent Application No. 58-122846).

(3) Method of stirring a dispersion of Mept compounds together with rigid body media having a particle size not larger than 0.2 mm in the presence of a salt of (metha)acrylic acid-stylene sulfonic acid copolymer having an average molecular weight of 10,000 to 1,000,000 (Japanese patent Application No. 59-82690)

Among the dispersants usable in the present invention, the condensation polymers (A) are curable condensation products obtainable from firstly reacting a polyamine compound having from 2 to 10 carbon atoms with an ether of polyoxyalkylene glycol having a terminal halogen or hydroxyl group and having from 2 to 4 carbon aooms in an alkylene unit thereof, further reacting the resulting polyamine reaction product having at least one hydrogen atom joined to a nitrogen atom with a bifunctional aliphatic compound aaving a functional group selected from the group consisting of epoxide and alpha-halo-beta-hydroxyalkyl. Alternatively, the thus obtained condnsation product may further be reacted with amines having saturated or unsaturated hydrocarbon group having 10 to 24 carbon atoms thereby obtaining a curable condensation product.

Preferable condensation polyeers are mentioned below.

(I) Reaction product of dipropylenetriamine, bischlorohydrin ether of polyoxyethylene glycol having an average molecular weight of about 1,000 and epichlorohydrin.

(II) Reaction product of dipropylenetriamine, bischlorohydrin ether of polyoxyethylene glycol having an average molecular weight of about 1,000, coconut oil fatty acid amine or beef tallow fatty acid amine and epichlorohydrin.

(III) Reaction product of dipropylenetriamine and bischlorohydrin ether of polyoxyethylene glycol having an average molecular weight of about 600.

(IV) Reaction product of dipropylenetriamine, bischlorohydrin ether of polyoxyethylene glycol having an average molecular weight of about 600, coconut oil fatty acid amine or beef tallow fatty acid amine.

(V) Reaction product of dipropylenetriamine, bischlorohydrin ether of polyoxyethylene glycol having an average molecular weight of about 1,000 and bischlorohydrin ether of polyoxyethylene glycol having an average molecular weight of about 600.

(VI) Reaction product of dipropylenetriamine, bischlorohydrin ether of polyoxyethylene glycol having an average molecular weight of about 1,000, bischlorohydrin ether of polyoxyethylene glycol having an average molecular weight of about 600 and coconut oil fatty acid amine or beef tallow fatty acid amine.

(VII) Reaction product of diethylenetriamine, ethoxylated ethylene chlorohydrin and epichlorohydrin.

(VIII) Reaction product of diethylenetriamine, ethoxylated ethylene chlorohydrin, epichlorohydrin, and coconut oil fatty acid amine or beef tallow fatty acid amine.

(IX) Reaction product of dipropylenetriamine, ethoxylated glycerine chlorohydrin ether and epichlorohydrin.

(X) Reaction product of dipropylenetriamine, ethoxylated glycerine chlorohydrin ether, epichlorohydrin and coconut oil fatty acid amine or beef tallow fatty acid amine.

(XI) Reaction product of triethylenetetramine, bischlorohydrin ether of polyoxyethylene glycol having an average molecular weight of about 1,000 and bischlorohydrin ether of polyoxyethylene glycol having an average molecular weight of about 600.

(XII) Reaction product of triethylenetetramine, bischlorohydrin ether of polyoxyethylene glycol having an average molecular weight of about 1,000, bischlorohydrin ether of polyoxyethylene glycol having an average molecular weight of about 600 and coconut oil fatty acid amine or beef tallow fatty acid amine.

(XIII) Reaction product of dipropylenetriamine and bischlorohydrin ether of polyoxyethylene glycol having an average molecular weight of about 200.

(XIV) Reaction product of dipropylenetriamine, bischlorohydrin ether of polyoxyethylene glycol having an average molecular weight of about 200 and coconut oil fatty acid amine or beef tallow fatty acid amine.

The ratio of the chlorine atoms to the hydrogen atoms of amino group in the reaction products of (I) to (XIV) is preferred to be in the range of 4:5 to 7:5.

Typical and preferable example of the condensation polymers is the product commercially sold under the trade name of Polyquart H from Henkel Co., Ltd., as a 50% aqueous solution.

Condensation polymers (A) are preferably incorporated in an amount of 1/100 to 10 times, more preferably 1/100 to 5 times of the fine particulate Mept compounds on the weight basis, and the balance is preferably an aqueous medium such as water or lower alcohol/water.

In the case where dispersant (A) is used, fine particulate Mept compounds should be incorporated in an amount of 0.0015 to 60%, and more preferably 0.1 to 50% of the total amount.

Examples of hydroxyalkyl celluloses of dispersant (B) of the invention include hydroxyethyl cellulose, hydroxypropyl cellulose and the like. Cationic cellulose derivatives obtainable by quaternarizing the hydroxyalkyl celluloses are preferably those represented by the following formula:

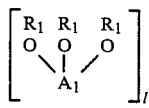

(1)

wherein $A_1$ represents a residue of anhydroglucose unit, $l$ represents an integer of from 50 to 20,000, and each $R_1$ represents a substitutional group represented by the following general formula (2):

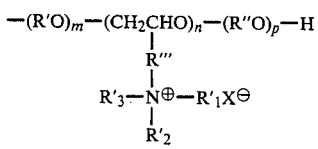

(2)

wherein

R′, R″: alkylene group having 2 or 3 carbon atoms, m: integer of from 0 to 10 n: integer of from 0 to 3 p: integer of from 0 to 10

R‴: alkylene group or hydroxyalkylene group having 1 to 3 carbon group, $R'_1$, $R'_2$, $R'_3$: same or different with each other and independently represent alkyl having up to 10 carbon atoms, aryl or aralkyl group, and may form a heterocyclic ring containing a nitrogen atom of the formula (2).

x: anion (chlorine, bromine, iodine, sulfuric acid, sulfonic acid, methylsulfuric acid, phosphoric acid, nitric acid etc.)

The cation substitution degree of the cationic celluloses preferably ranges from 0.01 to 1, in other words, average value of n per anhydroglucose unit is preferably 0.01 to 1, and more preferably, 0.02 to 0.5. Average value of m+p ranges from 1 to 3. Substiuution degree of 0.01 or less is insufficient. On the other hand, that of 1 or more is objectionable in view of the yield of the reaction. Molecular weight of the cationic celluloses usable in the present invention ranges from about 100,000 to 300,000.

Specific examples of the non-ionic surfactants of dispersant (B) are mentioned below.

(1) Polyoxyethylene alkyl or alkenyl ethers having an alkyl or alkenyl group having 10 to 20 carbon atoms on average and polyoxyethylene group having 1 to 20 units of ethylene oxide.

(2) Polyoxyethylene alkylphenyl ethers having an alkyl group having 6 to 12 carbonaatoms on average and polyoxyethylene group having 1 to 20 units of ethylene oxide.

(3) Polyoxypropylene alkyl or alkenyl ethers having an alkyl or alkenyl group having 10 to 20 carbon atoms on average and polyoxyprolylene group having 1 to 20 units of propylene oxide.

(4) Polyoxybutylene alkyl or alkenyl ethers having an alkyl or alkenyl group having 10 to 00 carbon atoms on average and polyoxybutylene group having 1 to 20 units of butylene oxide.

(5) Nonionic surface active agents having an alkyl or alkenyl group having 10 to 20 carbon atoms on average and added with 1 to 30 moles, in total, of ethylene oxide and propylene oxide or ethylene oxide and butylene oxide (arratio of ethylene oxide and propylene oxide or butylene oxide is in the range of 0.1/9.9 to 9.9/0.1).

(6) Higher fatty acid alkanolamides of the following formula or alkylene oxide adducts thereof

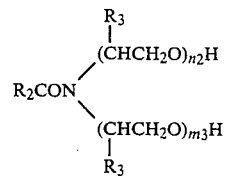

wherein $R_2$ represents an alkyl or alkenyl group having 7 to 21 carbon atoms, $R_3$ is a hydrogen atom or a methyl group, $n_2$ is an integer of 1 to 20, and m3 is an integer of 0 to 20, and hardened castor oil.

Examples of the cationic polymer compounds of dispersant (C) in the invention include the following compounds (a), (b) and (c), and they are used solely or in combination of two or more.

(a) Copolymer-type cationic polymer compounds of dimethyldiallylammonium halide and acryl amide:

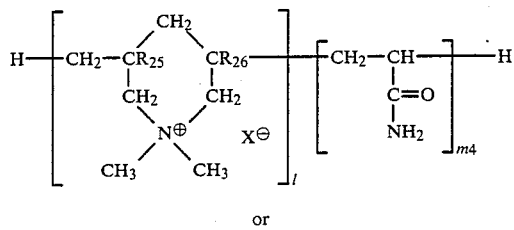

or

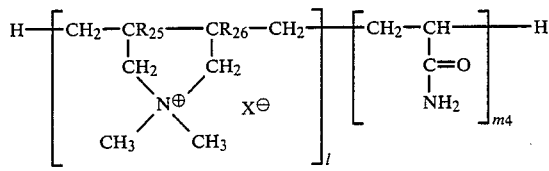

wherein $R_{25}$ and $R_{26}$ are the same or different with each other and independently represent a hydrogen atom or methyl, x represents a halogen atom, and $l$ and $m_4$ are such integers that the sum of $l$ and $m_4$ ranges from 180 to 2,000.

Although the compounds are represented by formula (a) here, they are not necesssarily a block-type copolymer, and arrangmment of the monomers may be arbitrary changed. Of these, compounds in which x is chlorine are sold under the tradename "Merquat 550" (Merck & Co., Inc./ U.S.A.)

(b) Polycondensation products of adipic acid and dialkylaminohydroxppropyl diethylenetriamine represented by the following formula and quaternarized products thereof:

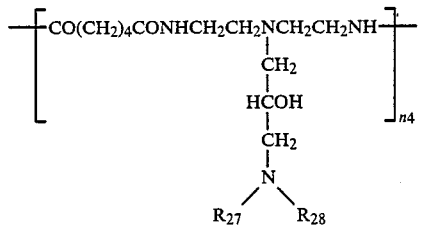

wherein $R_{27}$ and $R_{28}$ are the same or different with each other and independently represent an alkyl group having from 1 to 18 carbon atoms and $n_4$ represents such integer that will give the molecular weight ranging from 332 to 100,000.

Of these, those whose $R_{27}$ and $R_{28}$ are methyl are available from Sandoz Co., Ltd. under the tradename of "Cartaretin F".

(c) Copolymers represented by the following formula and quaternarized products thereof:

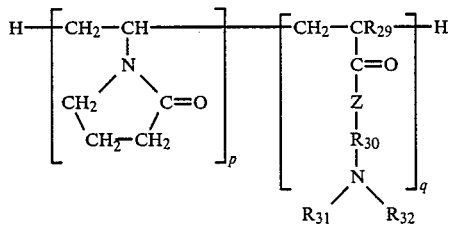

wherein $R_{29}$ represents a hydrogen atom, methyl group or ethyl group, Z represents an oxygen atom or a group —NH—, $R_{30}$ represents an alkylene group having 1 to 4 carbon atoms, $R_{31}$ and $R_{32}$ are the same or differnnt with each other and independently represent an alkyl group having 1 to 18 carbon atoms, and p and q are such integers that will give a molecular weight ranging from 1,000 to 5,000,000.

Although the compounds are represented by the above formula, they are not necessarily a block-type copolymer, and arrangement of the monomers may be changed arbitrarily. Of these, compounds in which Z is oxygen, $R_{29}$ is methyl, $R_{30}$ is ethylene, $R_{31}$ and $R_{32}$ are methyl and quaternarized by $(C_2H_5)_2SO_4$ are available from GAF Corporation under the tradenames of "Gafqurt 755" and "Gafqurt 734".

The inorganic salts sable as a member of dispersant (C) include alkali metal salts, alkaline earth metal salts or aluminum salts of an inorganic acid such as chloric acid, sulfuric acid, nitric acid and the like. Of these inorganic salts are preferred potassium sulfate, sodium sulfate, magnesium sulfate, aluminum sulfate, potassium nitrate, sodium nitrate, magnesium nitrate, calcium nitrate, aluminum nitrate, potassium chloride, sodium chloride, magnesium chloride, calcium chloride, aluminum chloride, potassium carbonate, sodium carbonate, aluminum carbonate. Among them, especially preferred ones are sodium sulfate, potassium nitrate, sodium nitrate, potassium chloride and sodium chloride.

The antimicrobial suspensions of the invention may be prepared according to conventional method by adding a powder of fine particulate Mept compounds or suspension thereof to a solution of the above-mentioned dispersants, but preferably be prepared by the following process.

Namely, the suspensioniis prepared by a method in which a powder of fine particulate Mept compounds is added to a 50% solution of dispersant (A) or a diluted solution thereof and agitated to give a uniform mixture, or by a method in which a dispersion of fine particulate Mept compounds is added to a 50% solution of dispersant (A) or a diluted solution thereof under agitation and further agitated to obtain a uniform mixture. The mixing is carried out using ordinary mixers such as propeller agitator apparatus, homogenizer mixers, sand mills and the like.

When dispersant (B) is used, the following four ingredients are processed as described below.

(1) 1 to 10% (as effective amount) of fine particulate Mept compounds, (2) Water-soluble polymer compound in an amount of 5 wt % or more of the fine particulate Mept compounds, (3) Non-ionic surfactant in an amount of 5 wt % or more of the water-soluble polymer compound, (4) Inon-exchanged water as balance. (First, 2) is dissolved in (4), then added with (3), followed by further addition of (1) under agitation until uniform mixture is obtained. Alternatively, (2) is dissolved in (4), then added with (1) and mixed well, followed by further addition of (3) under agitation until uniform suspension is obtained. The mixing apparatus usable in the process are ordinary ones as described before.

Further, in case where dispersant (C) is used for preparing an antimicrobial suspension, an aqueous solution comprising 0.1 to 60 wt %, preferably 1 to 50 wt % of a cationic polymer compound and 0.1 to 25 wt %, preferably 1 to 25 wt % of an inorganic salt should firstly be prepared. Examples of solvents are water or mixture of water and lower alcohol. Into the thus obtained aqueous solution, a dispersion comprising 0.1 to 60 wt %, preferably 0.1 to 50 wt % of fine particulate Mept compounds is added and agitated until uniform mixture is obtained. The mixing is carried out by a similar apparatus described before. The thus obtained antimicrobial suspensions can be used as it is. Optionally, they may be subjected to filtration under pressure, by which step, Mept particle having improved surface are obtainable.

Examples of antimicrobial hair treatment compositions according to the second invention include compositions for shampooes, hair rinses, hair lotions and the like. These compositions are prepared by incorporating the above described antimicrobial suspensions into a hair treatment bas under agitation and uniformly mixing them. The antimicrobial suspension should be incorporated in such an amount that the amount of fine particulate Mept compounds are 0.01 to 10 wt %, especially 0.05 to 5 wt % of the total composition.

The bases for hair treatments are those ordinarily used for these purposes. Among the hair treatment compositions, shampoo or hair rinse compositions are preferable in the practice of the invention. The bases for shampooes include anionic surfactants, amphoteric surfactants, cationic surfactants and mixtures thereof. Specific examples of these surfactants are mentioned below.

Anionic surfactants:

(1) Linear or branched alkylbenzenesulfonates having an alkyl group having 10 to 16 carbon atoms on average.

(2) Polyoxyalkylene alkyl ether sulfates having a linear or branched alkyl group having 8 to 20 carbon atoms on average and added with 0.5 to 8 moles of ethylene oxide and/or propylene oxide in one molecule thereof on average.

(3) Alkylsulfates having a linear or branched alkyl group having 10 to 20 carbon atoms on average.

(4) Olefinsulfonates having 10 to 20 carbon atoms in one molecule thereof on average.

(5) Alkanesulfonates having 10 to 20 carbon atoms in one molecule thereof on average.

(6) Fatty acid salts having a linear or branched, saturated or unsaturated hydrocarbon chain having 10 to 20 carbon atoms on average.

(7) Alkylethoxycarboxylates having a linear or branched alkyl group having 10 to 20 carbon atoms and added with 0.5 to 8 moles of ethylene oxide in one molecule thereof on average.

(8) Alkyl or alkenylsuccinates having an alkyl or alkenyl group having 6 to 20 carbon atoms on average and partially neutralized salts thereof.

(9) Phosphate aciive agents of the formula

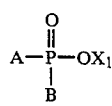

in which A represents

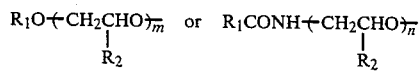

(in which $R_1$ represents a linear or branched, saturated or unsaturated hydrocarbon group, $R_2$ represents a hydrogen atom or a methyl group, m is an integer of from 0 to 6, and n is an integer of 1 to 6), B represents $-OX_2$ or A, and $X_1$ and $X_2$ independently represent a hydrogen atom or counter ion.

(10) Amino acid surface active agent of the formulae

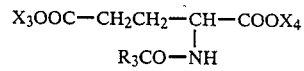

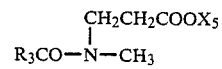

in which $R_3$ represents an alkyl or alkenyl group having 7 to 21 carbon atoms, $X_3$, $X_4$ and $X_5$ independently represent a hydrogen atom or counter ion.

(11) Acylated polypeptide surface active agents of the formula

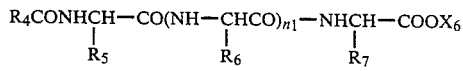

in which $R_4$ represents an alkyl or alkenyl group having 7 to 21 carbon atoms, $R_5$, $R_6$ and $R_7$ independently represent a side chain of an amino acid, $n_1$ is an integer of 1 to 6, and $X_6$ represents a hydrogen atom or counter ion.

The counter ions represented by $X_1$ to $X_6$ of these anionic surfactants generally include ions of alkali metals such as sodium, potassium and the like; alkaline earth metals such as magnesium; ammonium ion and alkanolamine bases having 1 to 3 alkanol groups having 2 or 3 carbon atoms such as, for example, monoethanolamine, diethanolamine, triethanolamine, triisopropanolamine and the like.

Amphoteric surfactants:

(12) Alkylamine oxides (I) and amidoamine oxides (II) of the following formulae

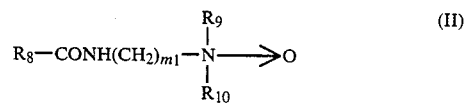

in which $R_8$ represents an alkyl or alkenyl group having 10 to 20 carbon atoms, $R_9$ and $R_{10}$ independently represent an alkyl group having 1 to 3 carbon atoms, and $m_1$ is an integer of 1 to 4.

(13) Alkyl or sulfobetaines (III) and amido or amidosulfobetaines (IV) of the following formulae

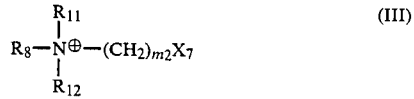

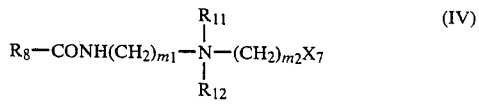

in which $R_{11}$ and $R_{12}$ independently represent an alkyl group having 1 to 4 carbon atoms, $m_2$ is an integer of 1 to 3, $X_7$ represents a $COO^\ominus$ or $-SO_3^{\ominus}$ group, $m_1$ and $R_8$ have the same meanings as defined before, respectively.

(14) Imidazoline amphoteric surface active agents of the following formula

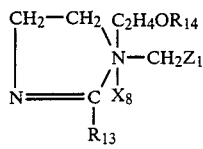

in which $R_{13}$ is an aliphatic acid residue having 10 to 20 carbon atoms on the average, $R_{14}$ represents sodium, hydrogen or $-CH_2COOM_2$, $Z_1$ represents

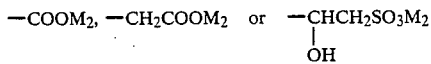

in which $M_2$ represents sodium, hydrogen or an organic base, $X_8$ represents a hydroxyl group, an acidic salt, an anionic surface active sulfate or a sulfated product.

(15) Amidoamine amphoteric surface active agents of the formula

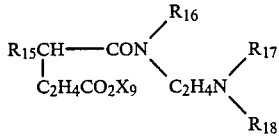

in which $R_{15}$ represents an alkyl or alkenyl group having 6 20 carbon atoms, $R_{16}$ represents hydrogen, $-C_2H_4OH$ or $-C_2H_4OC_2H_4COOX_9$, $R_{17}$ represents $-C_2H_4OH$, $-C_2H_4OC_2H_4COOX_9$ or $-C_2H_4COOX_9$, and $R_{18}$ represents hydrogen or $-C_2H_4COOX_9$, $X_9$ represents hydrogen, alkali metal, ammonium or organic ammonium.

Cationic surfactants:

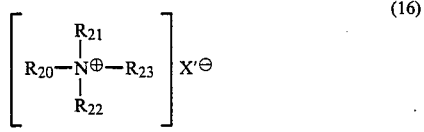

in which at least one of $R_{20}$, $R_{21}$, $R_{22}$ and $R_{23}$ represents an alkyl or alkenyl group having 8 to 24 carbon atoms and the other represent an alkyl group having 1 to 5 carbon atoms, and X' represents a halogen atom.

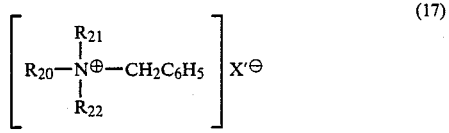

in which $R_{20}$, $R_{21}$, $R_{22}$ and X' have the same meanings as defined before, respectively.

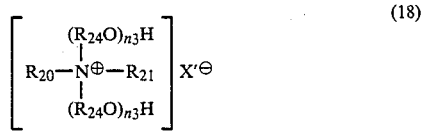

in which $R_{20}$, $R_{21}$ and X' have the same meanings as defined before, respectively, $n_3$ is an integer of 1 to 20, and $R_{24}$ represents an alkylene group having 2 to 3 carbon atoms.

It is to be noted that dispersant (B) requires a non-ionic suffactant as an essential component thereof, but when other dispersants are used, non-ionic surfactants may be incorporated as an arbitrary ingredient. Examples of the non-ionic surfactants include, aside from the before-mentioned polyoxyethylene alkyl or alkenyl ethers, polyoxyethylene alkylphenyl ethers, polyoxypropylene alkyl or alkenyl ethers, polyoxybutylene alkyl or alkenyl ethers, non-ionic surfactants obtainable by adding propyleneoxide or butylene oxide to ethylene oxide, and higher fatty acid alkanolamides or alkylene oxide adducts thereof, the following compounds are mentioned.

(19) Sucrose fatty acid esters obtainable from fatty acid having 10 to 20 carbon atoms on average and sucrose,

(20) Fatty acid glycerine monoester obtainable from fatty acid having 10 to 20 carbon atoms on average and glycerine.

Of these suractants, agents (1), (2), (3), (4), (5), (6), (11), (I) and (II) of (12), (13), (14), (15), polyoxyethylene alkyl or alkenyl ethers and higher fatty acid alkanolamides or alkyleneoxide adducts thereof are preferred. These surfactants may be used singly or in combination. Suitable amount of the surfactants is, for example, in the range not less than 5 wt %, preferably from 10 to 40 wt % in total, of the composition.

The antimicrobial hair treatment compositions may further comprise, aside from the above-described essential ingredients, any arbitrary ingredients ordinarily used for these purposes. Examples of such arbitrary ingredients include: solubilizers such as propylene glycol, glycerine, urea and the like; viscosity modifiers such as ethyl alcohol, isopropyl alcohol, methyl cellulose, higher alcohols and the like; preservatives; antiseborreheic agents; keratin-soluble or swelling substances such as sulfur, salicylic acid and enzymes; deodorants; pearling agents; lotionizing agents; perfumes; colorants; UV absorbers; antioxidants; preservatives and the like.

Action:

The function of the dispersants to be used in the present invention is not clear but it is considered that the dispersants make the particle surface of the fine particulate Mept compounds improved, thereby aggregation of the particles is prevented.

Effects of the Invention:

Several shampooes and hair rinses containing the Mept compounds are put on the market. However, in order to stably incorporate the Mept compounds into shampoo or hair rinse compositions, it is unavoidable to make them highly viscous or to add specific types of polymers or clay minerals. This leads to the disadvantage that the compositions become poor in performance, e.g. with shampooes, the foaming performance becomes poor with objectionable texture of the hair after shampooing.

Different from conventional method of modifying the viscosity of dispersion medium for improving the dispersion stability of Mept compounds, the inventive method utilizes fine particulate Mept compounds, thereby obtaining an antimicrobial suspension of very stable dispersion. Antimicrobial hair treatment compositions which incorporate fine particulate Mept compounds are excellent in storage stability and in feel on use.

Examples

The present invention is described by way of referential examples and examples.

The size distribution of Zpt in the referential examples or examples was determined by a centrifugal automatic size distribution measuring instrument CAPA-500 (available from K.K. Horiba Seisakusho). Water was used as a medium for dispersion. Density of the composition, viscosity and the specific gravity of Zpt patticles were 1, 0.8 cps (30° C.), and 1.78, respectively.

REFERENTIAL EXAMPLE 1

0.29 g of hepta hydride salt of zinc sulfate and 99.3 g of mixture of 1% solution of Polyquat H and water/ethanol (65/35) were charged in a reaction vessel and cooled down to −25° C., to which 0.75 g of aqueous 40% solution of sodium salt of 2-mercaptopyridine-N-oxide was charged at a time and reacted. After further 1 minute of agitation at the same temperature, the settled Zpt fine powder was collected. The size distribution of the fine particulate Zpt ss shown in Table 1.

TABLE 1

| Particle Size ($\mu$) | Distribution (wt %) | Cumulative Total (wt %) |
| --- | --- | --- |
| 1.00 < | 0.0 | 0.0 |
| 1.00–0.95 | 0.0 | 0.0 |
| 0.95–0.90 | 0.6 | 0.6 |
| 0.90–0.85 | 0.0 | 0.6 |
| 0.85–0.80 | 0.0 | 0.6 |
| 0.80–0.75 | 0.2 | 0.8 |
| 0.75–0.70 | 1.1 | 1.9 |
| 0.70–0.65 | 0.0 | 1.9 |
| 0.65–0.60 | 0.0 | 1.9 |
| 0.60–0.55 | 8.4 | 2.3 |
| 0.55–0.50 | 0.3 | 2.5 |
| 0.50–0.45 | 0.0 | 2.5 |
| 0.45–0.40 | 0.2 | 2.7 |
| 0.40–0.35 | 1.4 | 4.1 |
| 0.35–0.30 | 2.1 | 6.2 |
| 0.30–0.25 | 1.4 | 7.7 |
| 0.25–0.20 | 1.6 | 9.2 |
| 0.20–0.15 | 2.7 | 11.9 |
| 0.15–0.10 | 8.7 | 20.6 |
| 0.10–0.05 | 76.1 | 96.7 |
| 0.05–0.00 | 3.3 | 100.0 |
| Average Size | 0.08$\mu$ | |

REFERENTIAL EXAMPLE 2

70 ml of a commercially available Zpt dispersion (commercial product A having active ingredient of 50 wt %) and 130 ml of glass beads (media) having a size of 44 to 63 microns were mixed (media/dispersion ratio by volume=65/35) and placed in a 400 ml sand grinder (made by Igarashi Machine Manufacturing Co., Ltd.). Grinder discs were rotated for 3 hours at a peripheral speed of 5 m/sec. The temperature within the grinder was 20° to 25° C. The resulting dispersion was filtered under pressure to obtain 31 ml of fine particulate Zpt. The size distribution of thus obtained fine particulate Zpt is shown in Table 2.

TABLE 2

| Particle Size ($\mu$) | Distribution (wt %) | Cumulative Total (wt %) |
| --- | --- | --- |
| 0.90< | 0.0 | 0.0 |
| 0.90–0.84 | 0.0 | 0.0 |
| 0.84–0.78 | 0.0 | 0.0 |
| 0.78–0.72 | 1.4 | 1.4 |
| 0.72–0.66 | 3.3 | 4.7 |
| 0.66–0.60 | 0.0 | 4.7 |
| 0.60–0.54 | 2.4 | 7.1 |
| 0.54–0.48 | 1.9 | 9.0 |
| 0.48–0.42 | 2.8 | 11.8 |
| 0.42–0.36 | 4.3 | 16.1 |
| 0.36–0.30 | 5.7 | 21.8 |
| 0.30–0.24 | 7.3 | 29.1 |
| 0.24–0.18 | 12.5 | 41.6 |
| 0.18–0.12 | 22.2 | 63.8 |
| 0.12–0.06 | 32.9 | 96.7 |
| 0.06–0.00 | 3.3 | 100 |
| Average Size | 0.16$\mu$ | |

REFERENTIAL EXAMPLE 3

23 g of commercially available Zpt powder, 4.5 g of a water-soluble copolymer salt of the formula having a molecular weight of 680,000,

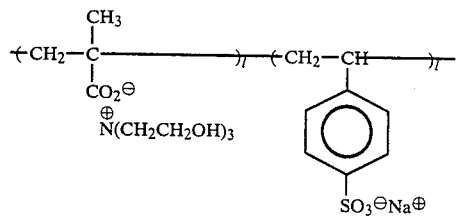

63 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 12 hours at a peripheral speed of 6 m/sec. The temperature in the sand grinder was found to be 20° to 25° C. The content was filtered under pressure to obtain 40 g of fine particulate Zpt dispersion. When the media are washed twice each with 70 g of water, 98% of Zpt could be recovered. The size distribution of thus obtained fine particulate Zpt is shown in Table 3.

TABLE 3

| Particle Size ($\mu$) | Distribution (wt %) | Cumulative Total (wt %) |
| --- | --- | --- |
| 0.90< | 0.0 | 0.0 |
| 0.90–0.84 | 0.0 | 0.0 |
| 0.84–0.78 | 0.0 | 0.0 |
| 0.78–0.72 | 0.0 | 0.0 |
| 0.72–0.66 | 0.0 | 0.0 |
| 0.66–0.60 | 0.0 | 0.0 |
| 0.60–0.54 | 0.8 | 0.8 |
| 0.54–0.48 | 0.0 | 0.8 |
| 0.48–0.42 | 1.0 | 1.8 |
| 0.42–0.36 | 0.1 | 1.9 |
| 0.36–0.30 | 1.4 | 3.3 |
| 0.30–0.24 | 4.2 | 7.5 |
| 0.24–0.18 | 3.0 | 10.5 |
| 0.18–0.12 | 7.4 | 17.9 |
| 0.12–0.06 | 20.2 | 38.2 |
| 0.06–0.00 | 61.8 | 100 |
| Average Size | 0.05$\mu$ | |

Example 1

Antimicrobial suspensions as shown in Table 1 were prepared by adding a certain amount of suspension containing Zpt in an amount of 50% to an aqueous solution of a water-soluble polymer of a predetermined concentration, and agitating the mixture. The appearance of the suspensions were observed immediately after the preparation, after 10 days storage at 25° C., after addition of sodium chloride (final concentration=3%, after 10 days of storage), and after frozen and remelted (from −20° C. to room temperature) by naked eyes. The results are shown in Table 4. In the table, symbols denote the following meanings.

o: uniform dispersion
F: flocculation
S: sedimentation
A: irreversible aggregation

TABLE 4

| | (wt %) | | | | | | | | | | | | | |
|---|---|---|---|---|---|---|---|---|---|---|---|---|---|---|
| | Inventive Products | | | | Comparative Products | | | | | | | | | |
| Antimicrobial Suspension | 1 | 2 | 3 | 4 | 1 | 2 | 3 | 4 | 5 | 6 | 7 | 8 | 9 | 10 |
| Fine Particulate Zpt Suspension (active ingredient 50%)[1] | 5 | 20 | 40 | 60 | | | 20 | | | 20 | 20 | 20 | 20 | 20 |
| Commercially Sold Zpt Suspension A (active ingredient 50%)[2] | | | | | 10 | | | 20 | | | | | | |
| Commercially Sold Zpt Suspension B (active ingredient 48%)[3] | | | | | | 10 | | | 20 | | | | | |
| Polyglycol/Polyamine Polycondensation Product (active ingredient 50%)[4] | 5 | 40 | 20 | 40 | 20 | 20 | | | | | | | | |
| Cationic Polymer Solution C (active ingredient 30%)[5] | | | | | | | | | | 50 | | | | |
| Cationic Polymer Solution D (active ingredient 40%)[6] | | | | | | | | | | | 38 | | | |
| Cationic Polymer Solution E (active ingredient 19%)[7] | | | | | | | | | | | | 80 | | |
| Hydroxyethyl Cellulose[8] | | | | | | | | | | | | | 10 | |
| Carboxyvinyl Polymer[9] | | | | | | | | | | | | | | 2 |
| Water | 90 | 40 | 40 | 0 | 70 | 70 | 80 | 80 | 80 | 30 | 42 | 0 | 70 | 78 |
| Appearance: | | | | | | | | | | | | | | |
| Immediately after the preparation | O | O | O | O | O | O | O | O | O | A | A | A | O | O |
| After storage for 10 days at 25° C. | O | O | O | O | S | S | O | S | S | — | — | — | O | O |
| Ten days after addition of 3% sodium chloride | O | O | O | O | S | S | F | F | F | — | — | — | A | A |
| After melting of frozen suspension | O | O | O | O | O | O | A | A | A | — | — | — | A | O |

[1]Product of Referential Example 2
[2]Size Distribution

| Particle Size ($\mu$) | Distribution (wt %) | Cumulative Total (wt %) |
|---|---|---|
| 2.00< | 0.0 | 0.0 |
| 2.00–1.90 | 0.0 | 0.0 |
| 1.90–1.80 | 0.6 | 0.6 |
| 1.80–1.70 | 7.7 | 8.3 |
| 1.70–1.60 | 4.1 | 12.4 |
| 1.60–1.50 | 0.6 | 13.0 |
| 1.50–1.40 | 0.0 | 13.0 |
| 1.40–1.30 | 0.0 | 13.0 |
| 1.30–1.20 | 0.6 | 13.6 |
| 1.20–1.10 | 2.8 | 16.4 |
| 1.10–1.00 | 0.0 | 16.4 |
| 1.00–0.90 | 1.9 | 18.3 |
| 0.90–0.80 | 9.0 | 27.3 |
| 0.80–0.70 | 1.4 | 28.7 |
| 0.70–0.60 | 4.6 | 33.3 |
| 0.60–0.50 | 9.8 | 43.1 |
| 0.50–0.40 | 11.9 | 55.0 |
| 0.40–0.30 | 16.1 | 71.1 |
| 0.30–0.20 | 17.8 | 88.9 |
| 0.20–0.10 | 9.5 | 98.4 |
| 0.10–0.00 | 1.6 | 100.0 |
| Average Size | 0.44$\mu$ | |

[3]Size Distribution

| Size ($\mu$) | Distribution (wt %) | Cumulative Total (wt %) |
|---|---|---|
| 3.00< | 0.0 | 0.0 |
| 3.00–2.85 | 0.0 | 0.0 |
| 2.85–2.70 | 2.1 | 2.1 |
| 2.70–2.55 | 1.3 | 3.4 |
| 2.55–2.40 | 0.0 | 3.4 |
| 2.40–2.25 | 1.9 | 5.3 |
| 2.25–2.10 | 3.1 | 8.4 |
| 2.10–1.95 | 2.7 | 11.1 |
| 1.95–1.80 | 1.5 | 12.6 |
| 1.80–1.65 | 1.0 | 13.6 |
| 1.65–1.50 | 1.5 | 15.1 |
| 1.50–1.35 | 9.6 | 24.7 |
| 1.35–1.20 | 14.4 | 39.1 |
| 1.20–1.05 | 5.6 | 44.7 |
| 1.05–0.90 | 6.3 | 51.0 |
| 0.90–0.75 | 7.9 | 58.9 |
| 0.75–0.60 | 9.0 | 67.9 |

TABLE 4-continued

| | | |
|---|---|---|
| 0.60–0.45 | 11.9 | 79.8 |
| 0.45–0.30 | 12.1 | 91.9 |
| 0.30–0.15 | 7.5 | 99.4 |
| 0.15–0.00 | 0.6 | 100.0 |
| Average Size | 0.91μ | |

(4) Polyquart H (Henkel Co., Ltd.)
(5) Polycondensation product of Adipic acid/Dimethylamino hydroxypropane diethylenetriamine (Cartaretin F, Sandoz Co., Ltd.)
(6) 1:1 Copolymer of methyldivinylimidazolium/vinylpyrrolidone (Luviquat FC 550, BASF Co., Ltd.)
(7) Copolymer of vinylpyrrolidone/dimethylaminoethylmethacrylate (Gafquat 755N, GAF Co., Ltd.)
(8) Average polymerization 1550
(9) Carbopol 941 (Goodrich Co., Ltd.)

As shown in Table 4, only inventive products incorporating fine particulate Zpt and condensation polymerization product of polyglycol/polyamine were excellent in lasting uniform suspension without any flocculation or sedimentation taken place under any condition.

EXAMPLE 2

A surfactant was added to water and dissolved to prepare a uniform solution having a final concentration referred to in Table 5. An antimicrobial suspension prepared in Example 1 was added to the resulting solution under agitation, further added with perfume and colorant. The pH was adjusted to 7 by citric acid, and the viscosity to 800 cps by ethanol, thereby obtaining shampoo compositions shown in Table 2. The appearance of the compositions were observed after 30 days storage at room temperature, at 50° C. and at 40° C., respectively, and after frozen and re-melted (from −20° C. to room temperature) by naked eyes. The results are shown in Table 5. The symboss have the same meanings as indicated in Example 1.

As shown in Table 5, only inventive shampoo compositions incorporating fine particulate Zpt and condensation polymerization product of polyglycol/polyamine were excellent in lasting stable suspension under any condition.

EXAMPLE 3

| Hair Rinse Composition: | |
|---|---|
| (1) Distearyldimethylammonium chloride | 2% |
| (2) Cetyl alcohol | 2 |
| (3) Propylene glycol | 3 |
| (4) Antimicrobial suspension (Inventive product 2, Zpt 10%) | 3 |
| (5) Perfume | 0.5 |
| (6) Colorant | small amount |
| (7) Citric acid | small amount |
| (8) Water | balance |

In a uniform solution of (1) and (8) was uniformly dispersed (4) and heated, followed by adding a hot uniform solution of (2) and (3) under agitation, cooling and adding (5), (6) and (7) to obtain a hair rinse composition. Thus obtained hair rinse composition was found to keep good and stable suspension over a long period without being flocculated or settled after heated or frozen and re-melted.

EXAMPLE 4

| Anti-dandruff Lotion: | |
|---|---|
| Fine particulate Zpt (50%) (obtained in Referential Example 2) | 4% |
| Polyquart H | 2.0 |
| Propylene glycol | 5 |
| Ethanol | 10 |
| Perfume | small amount |

TABLE 5

| | Inventive Products (wt %) | | | | | | Comparative Products | | | | |
|---|---|---|---|---|---|---|---|---|---|---|---|
| Shampoo Composition | 5 | 6 | 7 | 8 | 9 | 10 | 11 | 12 | 13 | 14 | 15 |
| Suspension of Antimicrobial Agent (Inventive Product 2, Zpt cont. 10%) | 10 | 10 | 10 | 10 | 20 | 5 | | | | | |
| Suspension of Antimicrobial Agent (Comparative Product 1, Zpt cont. 5%) | | | | | | | 20 | | | | |
| Suspension of Antimicrobial Agent (Comparative Product 3, Zpt cont. 10%) | | | | | | | | 10 | | | |
| Suspension of Antimicrobial Agent (Comparative Product 4, Zpt cont. 10%) | | | | | | | | | 10 | | |
| Suspension of Antimicrobial Agent (Comparative Product 9, Zpt cont. 10%) | | | | | | | | | | 10 | |
| Suspension of Antimicrobial Agent (Comparative Product 10, Zpt cont. 10%) | | | | | | | | | | | 10 |
| Sodium Polyoxyethylene(2.5)laurylether Sulfate (25%) | 60 | 40 | 40 | | 40 | | 60 | 60 | 60 | 40 | 60 |
| Triethanolamine Lauryl Sulfate (40%) | | | | 30 | | | | | | | |
| Sodium C$_{14,16}$-α-Olefinsulfonate (30%) | | | | | | 47 | | | | | |
| Imidazoline-type Amphoteric Surfactant (30%) | | 15 | | | | | | | | 15 | |
| Coconut Oil Fatty Acid Amidobetaine | | | 20 | | | | | | | | |
| Coconut Oil Fatty Acid Acyl-L-glutamic Triethanolamine | | | | 4 | | | | | | | |
| Sodium Lauroyl Sarcosinate | | | | | 6 | | | | | | |
| Coconut Oil Fatty Acid Diethanolamide | 3 | | | | | 3 | 3 | 3 | 3 | | 3 |
| Water and other additives | 27 | 35 | 30 | 56 | 34 | 45 | 17 | 27 | 27 | 35 | 27 |
| Appearance: | | | | | | | | | | | |
| Immediately after the preparation | O | O | O | O | O | O | O | O | O | A | A |
| After 30 days storage at Room Temperature | O | O | O | O | O | O | S | F | S | — | — |
| After 30 days storage at 50° C. | O | O | O | O | O | O | S | F | S | — | — |
| After 30 days storage at 40° C. | O | O | O | O | O | O | S | F | S | — | — |
| After melting of frozen suspension | O | O | O | O | O | O | O | F | O | — | — |

| -continued |  |
|---|---|
| Anti-dandruff Lotion: |  |
| Water | balance |

The procedure of Example 1 was followed to prepare an anti-dandruff lotion. The lotion was found to be stable over 1 month at room temperature. On the contrary, when no Polyquart H was used, Zpt was recognized to settle in 3 days.

EXAMPLE 5

| Aqueous Antimicrobial: |  |
|---|---|
| Fine particulate Zpt (50%) (obtained in Referential Example 2) | 0.2% |
| Polyquart H | 0.2 |
| Water | suitable amount |
| Total | 100 |

An aqueous antimicrobial was obtained in the same manner as in Example 2. The antimicrobial was stable over 1 month and showed good antimicrobial effects when applied to trees.

EXAMPLE 6

An antimicrobial dispersion of fine particulate Zpt of the following formulation was prepared, then diluted by ion-exchanged water and determined the size distribution by the centrifugal precipitation method. The results are shown in the sole FIGURE.

| (Formulation) |  |
|---|---|
| Hydroxyethylcellulose *1 | 1.2% |
| Zpt dispersion of Referential Example 2 (active ingredient 50 wt %) | 8 |
| Polyoxyethylene coconut oil fatty acid monoethanolamide *2 | 0.1 to 0.8 |
| Ion-exchanged water | balance |

(Note)
*1 HEC UNICEL QP 4400H, product of Daicel Chemical Industry Co., Ltd.
*2 Amizet 5C, product of Kawaken Fine Chemical Co., Ltd.

(Preparation)

Hydroxyethylcellulose was added to ion-exchanged water and heated to dissolve, followed by cooling down to room temperature, adding polyoxyethylene coconut fatty acid monoethanolamide to obtain a uniform mixture. Dispersion of fine particulate Zpt according to Referential Example 2 was added to the resulting mixture, and further agitated to obtain a uniform mixture.

EXAMPLE 7

| Shampoo Composition: (Formulation) |  |
|---|---|
| (1) Antimicrobial suspension according to Example 6 (containing Amizet 5C by 0.6%) | 25% |
| (2) Laurylsulfate triethanolamine salt (active ingredient 40%) | 40 |

| Shampoo Composition: (Formulation) |  |
|---|---|
| (3) Lauric acid diethanolamide | 3 |
| (4) Phosphoric acid | suitable amount |
| (5) Colorant | small amount |
| (6) Perfume | 0.5% |
| (7) Ethanol | suitable amount |
| (8) Ion-exchanged water | balance |

(Preparation)

In a uniform solution of (2) and (8) was dispersed (1) under agitation, and (3), (5) and (6) were further added under agitation until uniform mixture was obtained. (4) and (7) were added to the resulting solution in a suitable amount to adjust pH to 7, and vicosity to 200 cp (B-viscometer), thereby obtaining an antidandruff shampoo composition. This composition showed good dispersion after storage for 2 weeks at 40° C.

EXAMPLE 8

| Hair Rinse Composition: (Formulation) |  |
|---|---|
| (1) Antimicrobial suspension according to Example 6 (containing Amizet 5C by 0.6%) | 12.5% |
| (2) Stearyltrimethylammonium chloride | 3 |
| (3) Polyoxyethylene cetyl ether (EO 5) | 2 |
| (4) Liquid paraffin | 0.5 |
| (5) Isostearic acid | 0.5 |
| (6) Perfume | 0.5 |
| (7) Colorant | small amount |
| (8) Ion-exchanged water | balance |

(Preparation)

In a uniform solution of (2) and (8) was dispersed (1) under agitation until uniformly mixed, and (3), (4), (5), (6) and (7)wwere further added and mixed uniformly to prepare an antidandruff rinse composition. This composition showed good dispersion after storage for 2 weeks at 40° C.

EXAMPLES 9–16

Shampoo compositions shown in Table 6 were prepared following the methods of Examples 6 and 7. These products showed good dispersion after storage for 2 weeks at 40° C.

COMPARATIVE EXAMPLE

Comparative products 16 to 20 shown in Table 6 were prepared. Products which were not treated by water-soluble polymer/non-ionic surfactant were flocculated and sedimented. Commercially sold Zpt treated by water-soluble polymer/non-ionic surfactant showed sedimentation. The fine particulate Zpt which was not treated by non-ionic surfactant but was treated only by water-soluble polymer showed sedimentation. The fine particulate Zpt treated by methylcellulose/non-ionic surfactant showed sedimentation. The fine particulate Zpt treated by carboxymethylcellulose/non-ionic surfactant was flocculated and sedimented.

TABLE 6

| (wt %) | | | | | | | | | | | | |
|---|---|---|---|---|---|---|---|---|---|---|---|---|
| | Inventive Products | | | | | | | | Comparative Products | | | |
| | 11 | 12 | 13 | 14 | 15 | 16 | 17 | 18 | 16 | 17 | 18 | 19 | 20 |
| Antimicrobial Suspension*3 | | | | | | | | | | | | | |

TABLE 6-continued

| | (wt %) | | | | | | | | | | | | |
|---|---|---|---|---|---|---|---|---|---|---|---|---|---|
| | Inventive Products | | | | | | | | Comparative Products | | | | |
| | 11 | 12 | 13 | 14 | 15 | 16 | 17 | 18 | 16 | 17 | 18 | 19 | 20 |
| Zpt Dispersion of Referential Example 2 (active ingredient 50%) | 2 | 2 | 2 | 2 | 2 | 2 | 2 | 2 | 2 | 2 | | 2 | 2 |
| Commercially sold Zpt Dispersion (active ingredient 50%, 0.45 μm) | | | | | | | | | | | 2 | | |
| Hydroxyethyl Cellulose*4 | 0.2 | | | 0.2 | 0.2 | 0.2 | 0.2 | 0.2 | | 0.2 | 0.2 | | |
| Hydroxypropyl Cellulose*5 | | 0.2 | | | | | | | | | | | |
| Cationic Cellulose*6 | | | 0.2 | | | | | | | | | | |
| Methyl Cellulose*7 | | | | | | | | | | | | 0.2 | |
| Carboxymethyl Cellulose*8 | | | | | | | | | | | | | 0.2 |
| Polyoxyethylene(5) Coconut Oil Fatty Acid Monoethanolamide*9 | 0.1 | 0.1 | 0.1 | | | 0.1 | 0.1 | 0.1 | | 0.1 | 0.1 | 0.1 | |
| Polyoxyethylene(80) Hardened Castor Oil*10 | | | | 0.1 | | | | | | | | | |
| Secondary Alcohol E.O. Additive (EO90)*11 | | | | | 0.1 | | | | | | | | |
| Sodium Polyoxyethylene(2.5)laurylether Sulfate (active ingredient 25%) | 60 | 60 | 60 | 60 | 60 | | 40 | 40 | 60 | 60 | 60 | 60 | 60 |
| Sodium C14,16-α-olefinsulfonate (active ingredient 30%) | | | | | | 50 | | | | | | | |
| Coconut Oil Fatty Acid Diethanolamide | 3 | 3 | 3 | 3 | 3 | 3 | | | 3 | 3 | 3 | 3 | 3 |
| Sodium Lauroyl Sarcosinate | | | | | | | 5 | | | | | | |
| Coconut Oil Fatty Acid Monosodium Acyl-L-glutamate | | | | | | | | 5 | | | | | |
| Perfume | | | | | | | | 0.5 | | | | | |
| Colorant | | | | | | small amount | | | | | | | |
| pH modifier | | | | | | adjust pH to 7 | | | | | | | |
| Ethanol | | | | | | suitable amount to adjust viscosity of the shampoo composition to 200 cp. | | | | | | | |
| Water | | | | | | balance | | | | | | | |
| Stability after storage for 2 weeks at 40° C.*12 | O | O | O | O | O | O | O | O | F | S | S | S | F |

*3Prepared according to Example 6.
*4HEC UNICEL QP4400H (product of Daicel Chemical Industry Co., Ltd.)
*5HPC-M (product of Sanyo-Kokusaku Pulp Co., Ltd.)
*6Polymer JR 400
*7Metholose 60 SH (product of Shin-Etsu Chemical Co., Ltd.)
*8Daicel CMC #1260 (product of Daicel Chemical Industry Co., Ltd.)
*9Amizet 5C (product of Kawaken Fine Chemical Co., Ltd.)
*10HCO-80 (product of Nikko Chemical Co., Ltd.)
*11Softanol 90 (product of Nippon Shokubai K.K.)
*12Dispersion State
Uniform dispersion: O
Sedimentation: S
Flocculation: F

EXAMPLE 17

58 g of water, 15 g of sodium chloride and 17 g of cartaretin F (active ingredient 30%) were mixed up, followed by adding 10 g of fine particulate Zpt (active ingredient 50%) under agitation, and subjected to further agitation to obtain a suspension of fine particulate Zpt.

20 parts by weight (hereinafter simply referred to as parts) of the resulting suspension, which was in gel state, were added to 80 parts of sodium alkylether sulfate (active ingredient 2.5%) under agitation, and further mixed well, thereby obtaining a unioorm suspension. It was found to contain particles having as same size as measured prior to the treatment.

Zpt suspensions shown in Table 7 were prepared in the same manner as described above. Appearance of the suspension was observed after mixed with sodium alkylether sulfate under the same condition as mentioned above, and after 40 days storage at 25° C., respectively.

In the Table, "O", "A", "F" and "S" denote the following meanings respectively.
O: uniform suspension
A: Irreversible aggregation
F: Flocculation
S: sedimentation As shown in Table 7, inventive products 19 to 25 which make use of the compound selected from polycondensation product of adipic acid-dimethylaminohydroxypropyl diethylenetriamine, copolymerization product of dimethylamoniethyl methacrylate-vinylpyrrolidone and copolymerization product of dimethyldiallylammoniumchloride-acrylamide, inorganic salt and fine particulate Zpt gave excellent and uniform dispersion while keeping the size of fine particulate Zpt even in the presence of surfactants, and were not sedimented or irreversibly aggregated. On the contrary, comparative products 21 to 27 genarated flocculation or sedimentation, and were not agreeable.

TABLE 7

| | (wt %) Zpt Suspension No. | | | | | | | | | | | | | |
|---|---|---|---|---|---|---|---|---|---|---|---|---|---|---|
| | Inventive Products | | | | | | | Comparative Products | | | | | | |
| Component | 19 | 20 | 21 | 22 | 23 | 24 | 25 | 21 | 22 | 23 | 24 | 25 | 26 | 27 |
| Suspension of fine particulate Zpt according to Referential Example 2 (active ingredient 50%, average size 0.16μ) | 10 | 10 | 10 | 10 | 10 | 10 | 10 | 10 | 10 | 10 | | | 10 | 10 |
| Commercially sold Zpt Suspension (active ingredient 50%, average size 0.50μ) | | | | | | | | | | | 10 | 10 | | |
| Copolycondensation Product of Adipic Acid and Dimethyl-aminohydroxypropyl Diethylenetriamine (active ingredient 3%)*1 | 17 | 33 | 50 | 33 | | | | 33 | | | 33 | | | |
| Copolymerization Product of Dimethylaminoethyl-methacrylate and Vinylpyrrolidone (active ingredient 19%)*2 | | | | | 50 | | | | | | | | | |
| Copolymerization Product of Dimethylaminoethylmethacrylate and Vinylpyrrolidone | | | | | | 20 | | | 20 | | | 20 | | |

TABLE 7-continued

| | (wt %) Zpt Suspension No. | | | | | | | | | | | | | |
|---|---|---|---|---|---|---|---|---|---|---|---|---|---|
| | Inventive Products | | | | | | | Comparative Products | | | | | | |
| Component | 19 | 20 | 21 | 22 | 23 | 24 | 25 | 21 | 22 | 23 | 24 | 25 | 26 | 27 |
| (active ingredient 50%, Alcoholic Solution)*3 | | | | | | | | | | | | | | |
| Copolymerization Product of Dimethyldiallylammonium-chloride and Acrylamide (active ingredient 8%)*4 | | | | | | | 63 | | | 63 | | | | |
| Sodium Chloride | 15 | 15 | 15 | | 15 | 15 | 15 | | | | 15 | 15 | 15 | |
| Sodium Sulfate | | | | 7 | | | | | | | | | | |
| Water | 58 | 42 | 25 | 50 | 25 | 55 | 12 | 57 | 70 | 27 | 42 | 55 | 75 | 90 |
| Appearance: 80 parts of Sodium Polyoxyethylene (2.5) Lauryl Sulfate (active ingredient 25%) is added to 20 parts of the above described suspensions and stirred. | O | O | O | O | O | O | O | A | A | A | O | O | O | F |
| Appearance: After 40 days storage at 25° C. | O | O | O | O | O | O | O | — | — | — | S | S | F/S | F/S |

*1Cartaretin F (Sandoz Co.)
*2Gafquat 755 (GAF Corp.)
*3Gafquat 734 (GAF Corp.)
*4Merquat (Merck & Co., Inc.)

EXAMPLE 18

The method of Example 17 was followed to prepare Zpt suspensions shown in Table 8. The suspensions were added to 25% solution of sodium polyoxyethylene(2.5)lauryl sulfate. The apppearence of the dispersion was observed as in Example 17. The results are also shown in Table 8.

agitation, followed by further agitation until uniform mixture was obtained. The resulting mixture was added with perfume and colorant, adjusted pH to 7 by citric acid, and viscosity to 1,000–500 by ethanol.
*1: necessary amount for adjusting pH to 7
*2: necessary amount for modifying the viscosity in a range from 1,000 to 500
*3: Miranol C2M (Miranol Co. Ltd.)

TABLE 8

| | (wt %) Zpt Suspension No. Inventive Products | | | | | | | | | | | | | | |
|---|---|---|---|---|---|---|---|---|---|---|---|---|---|---|---|
| Component | 26 | 27 | 28 | 29 | 30 | 31 | 32 | 33 | 34 | 35 | 36 | 37 | 38 | 39 | 40 |
| Suspension of fine particulate Zpt according to Referential Example 2 (active ingredient 50%, average size 0.16μ) | 10 | 10 | 10 | 10 | 10 | 10 | 10 | 10 | 10 | 10 | 10 | 10 | 10 | 10 | 10 |
| Merquat 550 | 3.75 | 3.75 | 5 | 5 | | | | | | | | | | | |
| Gafquat 734 | | | | | 3.75 | 5 | | | | | | | | | |
| Gafquat 755 | | | | | | | 3.75 | 3.75 | 5 | 5 | | | | | |
| Cartaretin F | | | | | | | | | | | 3.75 | 5 | 5 | 6.25 | 6.25 |
| Sodium Chloride | 7.5 | 7.5 | 10 | 10 | 10 | 10 | 7.5 | 7.5 | 10 | 10 | 10 | 7.5 | 10 | 7.5 | 10 |
| Water | | | | | | | | Balance | | | | | | | |
| Appearance: 80 parts of Sodium Polyoxyethylene(2.5) Lauryl Sulfate is added to 20 parts of the above suspension and stirred. | O | O | O | O | O | O | O | O | O | O | O | O | O | O | O |
| Appearance: After 40 days storage at 25° C. | O | O | O | O | O | O | O | O | O | O | O | O | O | O | O |

EXAMPLE 19

Shampoo compositions shown in Table 9 were prepared making use of Zpt suspensions obtained in Example 17.

(preparation)
A surfactant, aqueous solution of a surfactant, and water were uniformly mixed, to which Zpt suspension prepared according to Example 17 was added under

*4: Rebon 2000 (Sanyo Kasei K.K.)

As shown in Table 9, inventive shampoo products 41 to 48 gave excellent suspension even after 2 month storages at room temperature, 40° C., and 50° C. without sedimented or flocculated. Further, after frozen and re-melted, the inventive products were found to restore good uuspension. On the contrary, comparative product 28 sedimented without flocculation, and comparative products 29 and 30 sedimented with flocculation.

TABLE 9

| | (wt %) Shampoo Composition No. | | | | | | | | | | |
|---|---|---|---|---|---|---|---|---|---|---|---|
| | Inventive Products | | | | | | | | Comparative Products | | |
| Component | 41 | 42 | 43 | 44 | 45 | 46 | 47 | 48 | 28 | 29 | 30 |
| Suspension of Inventive Product 20 | 20 | | | 20 | 20 | 20 | 20 | 20 | | | |
| Suspension of Inventive Product 24 | | 20 | | | | | | | | | |
| Suspension of Inventive Product 25 | | | 20 | | | | | | | | |
| Suspension of Comparative Product 24 | | | | | | | | | 20 | | |
| Suspension of Comparative Product 26 | | | | | | | | | | 20 | |
| Suspension of fine particulate Zpt (active ingredient 50%) | | | | | | | | | | | 20 |
| Sodium Polyoxyethylene(2.5) Lauryl Sulfate (active ingredient 25%) | 40 | 40 | 40 | | 40 | 40 | 40 | 40 | 40 | 40 | 40 |
| Sodium C$_{14-16}$-α-Olefinsulfonate (active ingredient 30%) | | | | 33 | | | | | | | |
| Coconut Oil Fatty Acid Diethanolamide | 5 | 5 | 5 | 5 | | | | | 5 | 5 | 5 |

TABLE 9-continued

| Component | Shampoo Composition No. (wt %) | | | | | | | | | | |
|---|---|---|---|---|---|---|---|---|---|---|---|
| | Inventive Products | | | | | | | | Comparative Products | | |
| | 41 | 42 | 43 | 44 | 45 | 46 | 47 | 48 | 28 | 29 | 30 |
| Imidazoline-type Amphoteric Surfactant (active ingredient 40%)*3 | | | | | 17 | | | | | | |
| Coconut Oil Fatty Acid Amidobetaine (active ingredient 30%)*4 | | | | | | 17 | | | | | |
| Sodium Lauroyl Sarcosinate | | | | | | | 5 | | | | |
| Monosodium Coconut Oil Fatty Acid Acyl-L-glutamate | | | | | | | | 5 | | | |
| Perfume | | | | | 0.5 | | | | | | |
| Colorant | | | | | Suitable Amount | | | | | | |
| Citric Acid | | | | | Suitable Amount*1 | | | | | | |
| Ethanol | | | | | Suitable Amount*2 | | | | | | |
| Water | | | | | Balance | | | | | | |
| Appearance: | | | | | | | | | | | |
| After storage for 2 months at Room Temperature | O | O | O | O | O | O | O | O | S | F | F |
| After storage for 2 months at 40° C. | O | O | O | O | O | O | O | O | S | F | F |
| After storage for 2 months at 50° C. | O | O | O | O | O | O | O | O | S | F | F |
| After melting of frozen suspension | O | O | O | O | O | O | O | O | O | F | F |

EXAMPLE 20

| Hair rinse Composition: (Formulation) | |
|---|---|
| Stearyltrimethyl ammonium chloride | 2 wt % |
| Cetyl alcohol | 3 |
| Propylene glycol | 3 |
| Zpt suspension (Inventive Product 20) | 5 |
| Perfume | 0.5 |
| Colorant | small amount |
| Citric acid | small amount |
| Water | balance |

Into a uniform solution of stearyltrimethyl ammoniumchloride and water was added and suspended a suspension of Inventive product 20 and heated, to which a uniform solution of cetyl alcohol and propylene glycol was added under further agitation. After cooling, perfume, colorant and citirc acid were added to prepare a hair rinse composition.

Thus obtained hair rinse compositions gave good suspension stability at room temperature, at 40° C., and at 50° C.

What is claimed is:

1. An antimicrobial suspension, comprising:
   (1) an antimicrobial effective amount of a fine particulate metal salt of 2-mercaptopyridine-N-oxide, Mept, wherein said metal is selected from the group consisting of magnesium, barium, strontium, zinc, cadmium, tin and zirconium, and wherein said particulate metal salt has a size distribution in which particles having a size below 0.2 μm are contained in amounts of at least 50 wt %, and has an average size below 0.16 μm, and
   (2) a dispersant or mixture of dispersants selected from the group consisting of (A), (B) and (C):
      (A) a polyglycol/polyamine condensation polymer, polyglycol/polyamine/alkylamine condensation polymer or alkyleneamine condensation polymer in an amount of from 1/100 to 10 times the fine particulate Mept compound on a weight basis;
      (B) a water-soluble polymer compound selected from the group consisting of hydroxyethylcellulose, hydroxypropylcellulose and quaternized derivatives thereof in an amount of 5 wt % or more of the fine particulate Mept compounds, and at least one nonionic surfactant in amounts of 5 wt % or more of the water-soluble polymer compound; and
      (C) at least one cationic polymer selected from the group consisting of the following compounds of (a), (b), and (c), an amount of said cationic polymer being from 0.1 to 60 wt % in an aqueous solution:
         (a) a copolymer-type cationic polymer compound of dimethyl diallylammonium halide and acrylamide represented by one of the following formulas:

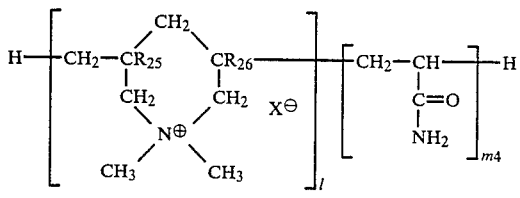

or

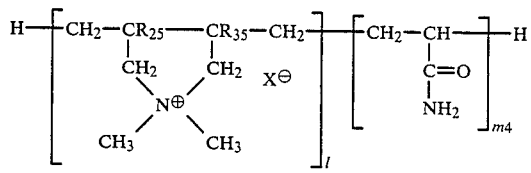

wherein $R_{25}$ and $R_{26}$ are the same or different and independently represent a hydrogen atom or methyl group, X represents a halogen atom, and $l$ and $m_4$ are integers such that the sum of $l$ and $m_4$ ranges from 180 to 2,000;
         (b) a polycondensation product of adipic acid and dialkylaminohydroxypropyl diethylenetriamine represented by the following formula or quaternized products thereof:

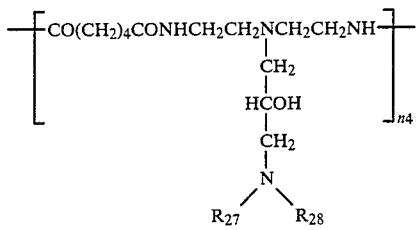

wherein, $R_{27}$ and $R_{28}$ are the same or different, and independently represent an alkyl group having 1 to 18 carbon atoms, and $n_4$ is an integer that gives a molecular weight of ranging from 332 to 100,000; and (c) a copolymer represented by the following formula or quaternized products thereof:

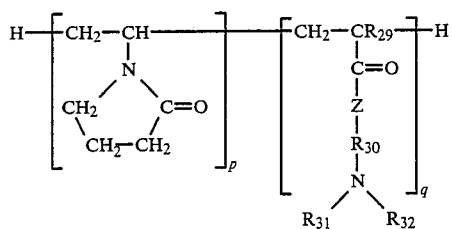

wherein, $R_{29}$ represents a hydrogen atom methyl group or ethyl group, Z represents an oxygen atom or a group —NH—, $R_{30}$ represents an alkylene group having 1 to 4 carbon atoms, $R_{31}$ and $R_{32}$ are the same or different and independently represent an alkyl group having 1 to 18 carbon atoms, and p and q independently represent integers that give a molecular weight ranging from 1,000 to 5,000,000, and an inorganic salt selected from the group consisting o alkali metal salts, alkaline earth metal salts, and aluminum salts of hydrochloric acid, sulfuric acid, or nitric acid in an amount of from 0.1 to 25 wt % in an aqueous solution.

2. The antimicrobial suspension according to claim 1, wherein said fine particulate polyvalent metal salt of 2-mercaptopyridine-N-oxide has a size distribution in which particles having a size below 0.2 micron are contained in amounts not smaller than 50 wt %, particles having a size ranging from 0.5 to 1.0 micron are contained 15 wt % or less, and particles having a size not smaller than 1.0 micron are contained 2 wt % or less.

3. The antimicrobial suspension according to claim 1, wherein said polyvalent metal salt of 2-mercaptopyridine-N-oxide is a zinc salt.

4. The antimicrobial suspension according to claim 1, wherein said polyvalent metal salt of 2-mercaptopyridine-N-oxide having a size distribution in which particles having a size below 0.2 micron are contained in amounts not smaller than 50 wt % is incorporated in said suspension by 0.0015 to 60 wt %, and said dispersant (A) is incorporated in said suspension by 1/100 to 10 times of the amount of said fine particulate polyvalent metal salt of 2-mercaptopyridine-N-oxide.

5. The antimicrobial suspension according to claim 1, wherein said fine particulate metal salt of 2-mercaptopyridine-N-oxide hss an average size of from 0.05 to 0.16 microns.

6. The antimicrobial suspension according to claim 1, wherein said fine particulate metal salt of 2-mercaptopyridine-N-oxide has an average size of from 0.05–0.08 microns.

7. An antimicrobial hai treatment composition containing an antimicrobial suspension, which comprises:

(1) an antimicrobial effective amount of a fine particulate metal salt of 2-mercaptopyridine-N-oxide, Mept, wherein said metal is selected from the group consisting of magnesium, barium, strontium, zinc, cadmium, tin and zirconium, and wherein said particulate metal salt has a size distribution in which particles having a size below 0.2 $\mu$m are contained in amounts of at least 50 wt %, and as an average size below 0.16 $\mu$m, and (2) a dispersant or mixture of dispersants selected from the group consisting of (A), (B) and (C):

(A) a polyglycol/polyamine condensation polymer, polyglycol/polyamine/alkylamine condensation polymer or alkyleneamine condensation polymer in an amount of from 1/100 to 10 times the fine particulate Mept compound on a weight basis;

(B) a water-soluble polymer compound selected from the group consisting of hydroxyethylcellulose, hydroxypropylcellulose and quaternized derivatives thereof in an amount of 5 wt % or more of the fine particulate Mept compounds, and at least one nonionic surfactant in amounts of 5 wt % or more of the water-soluble polymer compound; and (C) at least one cationic polymer selected from the group consisting of the following compounds of (a), (b), and (c), an amount of said cationic polymer being from 0.1 to 60 wt % in an aqueous solution:

(a) a copolymer-type cationic polymer compound of dimethyl diallylammonium halide and acrylamide represented by one of the following formulas:

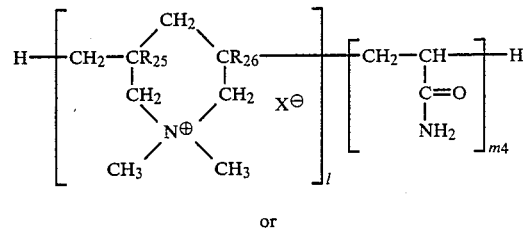

or

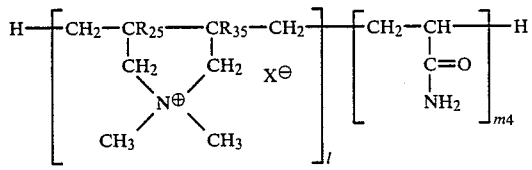

wherein $R_{25}$ and $R_{26}$ are the same or different and independently represent a hydrogen atom or methyl group, X represents a halogen atom, and l and $m_4$ are integers such that the sum of l and $m_4$ ranges from 180 to 2,000;

(b) a polycondensation product of adipic acid and diallylaminohydroxypropyl diethylenetriamine represented by the following formula or quaternized products thereof:

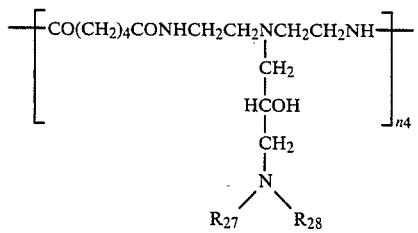

wherein $R_{27}$ and $R_{28}$ are the same or different, and independently represent an alkyl group having 1 to 18 carbon atoms, and $n4$ is an integer that gives a molecular weight of ranging from 332 to 100 000; and (c) a copolymer represented by the following formula or quaternized products thereof:

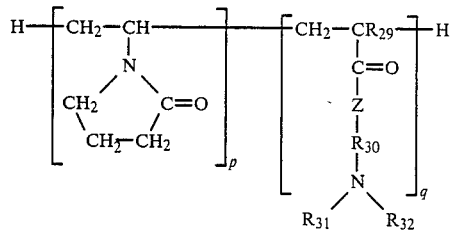

wherein $R_{29}$ rppresents a hydrogen atom, methyl group or ethyl group, Z represents an oxygen atom or a group —NH—, $R_{30}$ represents an alkylene group having 1 to 4 carbon atoms, $R_{31}$ and $R_{32}$ are the same or different and independently represent an alkyl group having 1 to 18 carbon atoms, and p and q independently represent integers that give a molecular weight ranging from 1,000 to 5,000,000, and an inorganic salt selected from the group consisting of alkali metal salts, alkaline earth metal salts, and aluminum salts of hydrochloric acid, sulfuric acid, or nitric acid in an amount of from 0.1 to 25 wt % in an aqueous solution.

8. The hair treatment composition according claim 7, wherein said composition is a shampoo composition or a hair rinse composition.

9. An antimicrobial hair treatment composition according to claim 7 or claim 8, wherein said hair treatment composition comprises a surfactant for shampoo use containing a mixture of one or more agents selected from the group consisting of anionic surfactants, amphoteric surfactants, non-ionic surfactants and cationic surfactants.

10. The antimicrobial hair treatment composition according to claim 9, wherein said surfactant for shampoo use is contained in an amount of 5 wt % or more based on the total composition.

* * * * *